United States Patent
Inosaka et al.

(10) Patent No.: US 6,231,883 B1
(45) Date of Patent: May 15, 2001

(54) HIGH MOLECULAR-WEIGHT MEDICAL ADHESIVE WITH PLASTICIZERS, AND PRODUCT THEREOF

(75) Inventors: Keigo Inosaka; Takateru Muraoka; Hitoshi Akemi; Saburo Otsuka; Yuichi Inoue, all of Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 09/117,000

(22) Filed: Jul. 17, 1998

(30) Foreign Application Priority Data

Jul. 17, 1997 (JP) .................................................. 9-192894
Jul. 10, 1998 (JP) ................................................. 10-195375

(51) Int. Cl.[7] .............................. A61L 15/24; A61L 15/58
(52) U.S. Cl. ......................... 424/443; 424/449; 424/447; 524/315; 524/560
(58) Field of Search .................................... 524/315, 560; 424/449, 443, 447

(56) References Cited

U.S. PATENT DOCUMENTS

| | | |
|---|---|---|
| 4,750,482 | 6/1988 | Sieverding . |
| 5,176,916 * | 1/1993 | Yamanka et al. ..................... 424/448 |
| 5,556,636 * | 9/1996 | Yano et al. ............................ 424/448 |
| 5,645,855 * | 7/1997 | Lorenz ................................. 424/449 |

FOREIGN PATENT DOCUMENTS

| | | | |
|---|---|---|---|
| 0201102A2 * | 12/1986 | (EP) | ............................ C08F/220/12 |
| 0 661 302 | 7/1995 | (EP) . | |
| 0 711 551 | 5/1996 | (EP) . | |

OTHER PUBLICATIONS

WO 98 13035 Abstract, Apr. 2, 1998 (Derwent Publications Ltd., AN 1998–286399 XP002143206).

* cited by examiner

*Primary Examiner*—David W. Wu
*Assistant Examiner*—Kelechi C. Egwim
(74) *Attorney, Agent, or Firm*—Sughrue, Mion, Zinn, Macpeak & Seas, PLLC

(57) ABSTRACT

A medical adhesive sheet comprising a support and an adhesive layer formed on one side of said support, wherein the adhesive layer comprises an adhesive polymer having a weight average molecular weight of not less than 2,000,000, preferably not less than 2,500,000, and at least one plasticizer compatible with said polymer. The medical adhesive sheet of the present invention simultaneously satisfies the adhesive property to the skin and low irritation property, since it can retain the plasticizer in the adhesive layer, even without a crosslinking treatment. The effects of the present invention can be exerted irrespective of the kind of functional group that the plasticizer and drug have.

17 Claims, No Drawings

HIGH MOLECULAR-WEIGHT MEDICAL ADHESIVE WITH PLASTICIZERS, AND PRODUCT THEREOF

TECHNICAL FIELD OF THE INVENTION

The present invention relates to a medical adhesive sheet to be adhered to the skin surface to cover the skin for protection and to continuously administer a drug into a body through the skin, and to the production thereof.

BACKGROUND OF THE INVENTION

Various skin surface adhesion type external agents have been heretofore developed, inclusive of one for covering the surfaces of healthy skin and wounded skin for protection and one for percutaneous administration of a drug into a body through the skin. Since these external agents are adhered to the skin surface, they are required to have superior handling property in application, skin surface movement-following capability, and low irritation to the skin to suppress damages to keratin.

Of these, handling property in application and low irritation to the skin can be dealt with by altering the composition of the adhesive itself to appropriately decrease the adhesive power to the skin or by adding a liquid component (e.g., water and oily component) to the adhesive layer to make a water-containing gel or oily gel, thereby imparting softness to the adhesive layer. In the latter method, a crosslinking agent may be also used to impart a cohesive power to the adhesive to retain the liquid component in the adhesive layer. This crosslinking agent reacts, at plural sites, with the functional group that the adhesive possesses, such as carboxyl group, hydroxyl group and amino group. As a result, the adhesive layer has a net structure that enables retention of the liquid component. In this reaction, when the liquid component, additive, drug and the like have a functional group capable of reacting with the crosslinking agent, the crosslinking agent first reacts with them rather than with the adhesive, because they have low molecular weights and superior dispersibility, and this tends to occur actually. Consequently, due to the absence of crosslinking of the adhesive by the action of a crosslinking agent, the liquid component cannot be retained in the adhesive layer and the inherent effects of the liquid component, additive, drug and the like cannot be exerted.

The present invention aims at solving the above-mentioned problems, and achieves low irritation property by retaining a liquid component in an adhesive layer, and provides a production method thereof.

SUMMARY OF THE INVENTION

As a result of the studies in an attempt to retain a liquid component in an adhesive layer without using a crosslinking agent, the present invention can solve the above-mentioned problems by the use of a polymer having a weight average molecular weight of not less than 2,000,000 as an adhesive. Thus, the present invention provides the following.

(1) A medical adhesive sheet comprising a support and an adhesive layer formed on one side of said support, wherein the adhesive layer comprises an adhesive polymer having a weight average molecular weight of not less than 2,000,000 and at least one plasticizer compatible with said polymer.

(2) The medical adhesive sheet of above (1), wherein the adhesive polymer has a weight average molecular weight of not less than 2,500,000.

(3) The medical adhesive sheet of above (1), wherein the adhesive polymer has a weight average molecular weight of not less than 5,000,000.

(4) The medical adhesive sheet of above (1), wherein the adhesive polymer is an acrylate type polymer.

(5) The medical adhesive sheet of above (4), wherein the acrylate type polymer is a copolymer obtained by copolymerizing alkyl (meth)acrylate as a main component.

(6) The medical adhesive sheet of above (1), wherein the plasticizer is a liquid plasticizer.

(7) The medical adhesive sheet of above (6), wherein the liquid plasticizer is contained in a proportion of 10–100 parts by weight per 100 parts by weight of the adhesive polymer.

(8) The medical adhesive sheet of above (6), wherein the liquid plasticizer is a fatty acid ester obtained by reacting a higher fatty acid having 12 to 16 carbon atoms and a lower monovalent alcohol having 1 to 4 carbon atoms.

(9) The medical adhesive sheet of above (1), wherein the plasticizer comprises a liquid plasticizer and a solid plasticizer.

(10) The medical adhesive sheet of above (9), wherein the liquid plasticizer is contained in a proportion of 10–100 parts by weight per 100 parts by weight of the adhesive polymer.

(11) The medical adhesive sheet of above (9), wherein the liquid plasticizer is a fatty acid ester obtained by reacting a higher fatty acid having 12 to 16 carbon atoms and a lower monovalent alcohol having 1 to 4 carbon atoms, or a combination of said fatty acid ester, a fatty acid having 8 to 10 carbon atoms and glycerol.

(12) The medical adhesive sheet of above (9), wherein the solid plasticizer is contained in a proportion of not more than 10 parts by weight per 100 parts by weight of the adhesive polymer.

(13) The medical adhesive sheet of above (9), wherein the solid plasticizer is a monoglyceride obtained by reacting a fatty acid having 8 to 10 carbon atoms and glycerol.

(14) The medical adhesive sheet of above (1), wherein the adhesive layer further contains a drug for percutaneous absorption.

(15) A method for producing a medical adhesive sheet, which comprises (a) applying a solution containing a composition comprising an adhesive polymer having a weight average molecular weight of not less than 2,000,000 and at least one plasticizer compatible with said polymer, on one surface of a support and (b) drying same to form an adhesive layer.

(16) The method of above (15) wherein the adhesive polymer is prepared by emulsion polymerization.

DETAILED DESCRIPTION OF THE INVENTION

The medical adhesive sheet of the present invention has an adhesive layer formed on one surface of a support. The support to be used in the present invention is not particularly limited, but a material through which a plasticizer and a drug do not permeate to decrease their contents, namely, a material impervious to these components is preferable. Specific examples thereof include a film made from polyester, nylon, poly(vinyl chloride), polyethylene, polypropylene, ethylene-vinyl acetate copolymer, polytetrafluoroethylene, ionomer resin and the like, a metal foil, and a laminate film made therefrom. In particular, the support is preferably a laminate film of a non-porous film made from the above-mentioned materials and a porous film, and the adhesive layer is preferably formed on the side of the porous film, so that the adhesion (anchor property) between the support and the adhesive layer can be improved.

While the porous film is not particularly limited as long as the adhesive layer has superior anchor property, preferred are paper, woven fabric, nonwoven fabric, mechanically perforated sheet and the like, with particular preference given to paper, woven fabric and nonwoven fabric. The thickness of the porous film is 10–100 µm, and about 10–200 µm in the case of a thin medical adhesive sheet of a plaster type or an adhesive tape type, in consideration of an improved anchor property and flexibility of the medical adhesive sheet. When it is a woven or nonwoven fabric, the basic weight is 5–30 g/m$^2$, preferably 8–20 g/m$^2$, for an improved anchor property.

The adhesive layer to be formed on one surface of a support contains an adhesive polymer and a plasticizer compatible with said polymer. The adhesive polymer has a weight average molecular weight of not less than 2,000,000, preferably not less than 2,500,000, more preferably not less than 5,000,000. The use of such high molecular weight adhesive polymer as an adhesive permits the plasticizer to be retained in the adhesive layer, due to the cohesive power that this adhesive polymer has. When the molecular weight is less than 2,000,000, the above-mentioned adhesive polymer has less cohesive power, so that the plasticizer is not retained in the adhesive layer but bloomed on the surface of the adhesive layer to impair adhesive property. The upper limit of the weight average molecular weight of the above-mentioned polymer is about 10,000,000.

A polymer having a weight average molecular weight of not less than 2,000,000 is produced by emulsion polymerization, bulk polymerization or suspension polymerization. Of these, emulsion polymerization is preferably used, since the weight average molecular weight can be adjusted rather easily.

The weight average molecular weight as referred to in the present invention is determined by dissolving a polymer in a determination solvent, such as tetrahydrofuran or dimethyl sulfoxide, followed by detection by gel permeation chromatography (GPC) using a differential refraction system.

The adhesive polymer is not particularly limited as long as it has a weight average molecular weight of not less than 2,000,000 and is compatible with the plasticizer to be mentioned later. Preferred are acrylate type polymers, particularly a copolymer obtained by copolymerizing alkyl (meth)acrylate as a main component. Examples of alkyl (meth)acrylate include those wherein alkyl is a straight or branched alkyl having 4 or more carbon atoms, such as butyl, pentyl, hexyl, heptyl, octyl, nonyl, decyl, undecyl, dodecyl and tridecyl. They may be used alone or in combination.

The monomer copolymerizable with the above-mentioned alkyl (meth)acrylate may be, for example, monomers having a carboxyl group, such as (meth)acrylic acid, itaconic acid, maleic acid and maleic anhydride; monomers having a sulfo group, such as styrenesulfonic acid, allylsulfonic acid, sulfopropyl(meth)acrylate, (meth)acryloyloxynaphthalene sulfonic acid and acrylamide methylpropanesulfonic acid; monomers having a hydroxyl group, such as hydroxyethyl (meth)acrylate and hydroxypropyl (meth)acrylate; (meth) acrylic acid derivatives having an aide group, such as (meth)acrylamide, dimethyl (meth)acrylamide, N-butyl (meth)acrylamide and N-methylol(meth)acrylamide; aminoalkyl (meth)acrylates, such as aminoethyl (meth)acrylate, dimethylamino ethyl (meth)acrylate and t-butylaminoethyl (meth)acrylate; alkoxyalkyl (meth)acrylates, such as methoxyethyl (meth)acrylate, ethoxyethyl (meth)acrylate and tetrahydrofurfuryl (meth)acrylate; alkoxyalkylene glycol (meth)acrylates, such as methoxyethylene glycol (meth) acrylate, methoxydiethylene glycol (meth)acrylate, methoxypolyethylene glycol (meth)acrylate and methoxypolypropylene glycol (meth)acrylate; (meth)acrylonitrile; and compounds having a vinyl group, such as vinyl acetate, vinyl propionate, N-vinyl-2-pyrrolidone, methylvinyl pyrrolidone, vinyl pyridine, vinyl piperidone, vinyl pyrimidine, vinyl piperadine, vinyl pyrazine, vinyl pyrrole, vinyl imidazole, vinyl caprolactam, vinyl oxazole and vinyl morpholine, which may be used alone or in combination. The amount of these monomers to be copolymerized is changed depending on the weight average molecular weight of the copolymer to be obtained.

Even when the adhesive polymer is other than the above-mentioned acrylate polymers and is a silicone polymer or a rubber polymer, such as polyisobutylene polymer, styrene-butadiene polymer, styrene-isoprene-styrene polymer and the like, it is applicable as long as the compatibility with the plasticizer and solubility and releasability of the drug are sufficient.

The plasticizer to be added to the adhesive layer plasticizes the adhesive layer to impart softness, thereby decreasing irritation to the skin. The plasticizer to be used in the present invention is free of limitation as long as it shows plasticizing action and is compatible with the above-mentioned adhesive polymer. It preferably improves percutaneous absorption of the drug and storage stability. A plasticizer that is liquid at room temperature (hereinafter also referred to as a liquid plasticizer) is preferably used. Examples of the liquid plasticizer include fatty acid ester obtained by reacting a higher fatty acid having 12 to 16 carbon atoms and lower monovalent alcohols having 1 to 4 carbon atoms; fatty acids having 8 to 10 carbon atoms; glycols, such as ethylene glycol, diethylene glycol, triethylene glycol, polyethylene glycol, propylene glycol and polypropylene glycol; fats and oils, such as olive oil, castor oil, squalene and lanolin; organic solvents, such as ethyl acetate, ethyl alcohol, dimethyldecyl sulfoxide, methyloctyl sulfoxide, dimethyl sulfoxide, dimethylformamide, dimethylacetamide, dimethyllaurylamide, dodecylpyrrolidone and isosorbitol; liquid surfactants; plasticizers conventionally known, such as diisopropyl adipate, phthalic acid ester and diethyl sebacate; hydrocarbons, such as liquid paraffin; and others such as ethoxy stearyl alcohol, glycerol ester, isopropyl myristate, isotridecyl myristate, ethyl laurate, N-methyl pyrrolidone, ethyl oleate, oleic acid, diisopropyl adipate, diisopropyl palmitate, octyl palmitate, 1,3-propanediol, glycerol and the like. They may be used alone or in combination. It is needless to say that those that are liquid at normal temperature can be used.

Of the above-mentioned liquid plasticizers, fatty acid esters obtained by reacting a higher fatty acid having 12 to 16 carbon atoms and a lower monovalent alcohol having 1 to 4 carbon atoms is preferable, in view of compatibility with the adhesive polymer, adequate adhesion to the skin and absence of volatilization during heating. The higher fatty acid having 12 to 16 carbon atoms is exemplified by lauric acid, myristic acid and palmitic acid; and lower monovalent alcohol having 1 and 4 carbon atoms is exemplified by methyl alcohol, ethyl alcohol, propyl alcohol and isopropyl alcohol. Particularly preferred is isopropyl myristate.

Considering the percutaneous absorption of the drug, fatty acids having 8 to 10 carbon atoms and glycerol may be also added besides the above-mentioned fatty acid esters. Examples of the fatty acid having 8 to 10 carbon atoms include caprylic acid (octoic acid, C8), pelargonic acid (nonanoic acid, C9) and capric acid (decanoic acid, C10).

The liquid plasticizer is preferably added in a proportion of 10–100 parts by weight, more preferably 60–100 parts by weight, per 100 parts by weight of the above-mentioned adhesive polymer. When it is less than 10 parts by weight, the adhesive layer is insufficiently plasticized and sufficient reduction of irritation to the skin cannot be achieved. When it exceeds 100 parts by weight, the liquid plasticizer may not be retained in the adhesive layer by the cohesive power of the adhesive polymer, and may be bloomed on the surface of the adhesive layer, causing poor adhesive property.

As the plasticizer, a plasticizer that is solid at room temperature (hereinafter also referred to as a solid plasticizer) may be added besides the liquid plasticizer. This solid plasticizer in the adhesive layer is compatible with the above-mentioned adhesive polymer and liquid plasticizer, and loses its solidness during use.

The solid plasticizer may be, for example, monoglycerides obtained by reacting a fatty acid having 8 to 10 carbon atoms and glycerol; acrylate copolymers and other polymers; stabilizers (antioxidants), such as ascorbic acid, L-ascorbic acid, stearic acid ester and L- or DL-alanin; higher fatty acids having 11 or more carbon atoms, such as lauric acid, myristic acid and palmitic acid; and fatty acid esters of glycerol that are solid (wax state) at normal temperature. These may be used alone or in combination. It is needless to say that those that are solid at normal temperature are used.

Of the above-mentioned solid plasticizers, monoglycerides obtained by reacting a fatty acid having 8 to 10 carbon atoms and glycerol are preferably used, in view of compatibility with the adhesive polymer, adequate adhesion to the skin and absence of volatilization during heating. Examples of the fatty acid having 8 to 10 carbon atoms include caprylic acid (octoic acid, C8), pelargonic acid (nonanoic acid, C9) and capric acid (decanoic acid, C10).

The solid plasticizer is preferably added in a proportion of not more than 10 parts by weight, more preferably not more than 5 parts by weight, per 100 parts by weight of the above-mentioned adhesive polymer. When it exceeds 10 parts by weight, the liquid plasticizer and solid plasticizer may not be retained in the adhesive layer by the cohesive power of the adhesive polymer. Thus, blooming may occur on the surface of the adhesive layer, thereby degrading the adhesive property. The lower limit is the level permitting plasticization of the adhesive layer and is about 0.01 part by weight.

In concurrent use, the liquid plasticizer and solid plasticizer are preferably added in a weight ratio of liquid plasticizer:solid plasticizer of 1:0.02–1:0,20, more preferably 1:0.04–1:0.18, and the total amount of the liquid plasticizer and solid plasticizer is preferably 20–100 parts by weight, more preferably 40–90 parts by weight, per 100 parts by weight of the above-mentioned adhesive polymer.

The adhesive layer may further contain a drug for percutaneous absorption. The percutaneously absorbable drug to be used in the present invention is appropriately selected according to the treatment purposes, and may be, for example, corticosteroids, analgesic inflammatory agents, hypnosedatives, tranquilizer, antihypertensive agents, hypotensive diuretics, antibiotics, anesthetics, antibacterial agents, antifungus agents, vitamins, coronary vasodilating agents, antihistaminics, antitussives, sex hormones, antidepressant, cerebral circulation improving agents, antiemetic drugs, antitumor agents, biological medicines and the like, which are capable of being absorbed through the skin. These drugs may be used in combination where necessary. Of these, a hydrophobic drug (not more than 0.4 g being dissolved in 100 g of water) is preferable in view of uniform dispersibility in the adhesive layer and percutaneous absorption.

The contents of these drugs are appropriately determined depending on the kind of drug for percutaneous absorption and administration purposes. It is preferably 1–40%, more preferably 3–30%, of the adhesive layer. When it is less than 1 wt %, a therapeutically effective amount of the drug cannot be released, and when it exceeds 40 wt %, therapeutic effects are limited and such a large content is economically disadvantageous.

The thickness of the adhesive layer is preferably 10–200 μm, more preferably 30–100 μm, in consideration of the adhesive property, and when a percutaneously absorbable drug is contained, additionally in consideration of the necessary amount thereof and utilization efficiency.

The inventive medical adhesive sheet can be prepared by mixing an adhesive polymer having a weight average molecular weight of not less than 2,000,000 and at least one plasticizer, and when used for the prevention and treatment of various diseases, a percutaneously absorbable drug in, where necessary, a solvent, applying this solution onto a separator, so that the thickness after drying is preferably 10–200 μm, more preferably 30–100 μm, drying same to give an adhesive layer, and transferring this adhesive layer onto one surface of a support.

The medical adhesive sheet of the present invention can be appropriately used as a medical adhesive sheet to cover skin surface for protection, such as bandages and dressings, and when containing a percutaneously absorbable drug, it can be used as a medical adhesive sheet for the prevention and treatment of various diseases.

Due to the addition of a plasticizer to a polymer having superior adhesive property, the inventive medical adhesive sheet has an adequately-decreased adhesive property of the adhesive layer, and softness by plasticization of the adhesive layer, thereby achieving low irritation property of the medical adhesive sheet, According to the present invention, a high molecular weight polymer having a weight average molecular weight of not less than 2,000,000 is used as the adhesive polymer. Since this polymer has a high cohesive power, it can retain a plasticizer in an adhesive layer only by the cohesive power of the adhesive polymer, even without a conventional crosslinking treatment. Therefore, the medical adhesive sheet of the present invention simultaneously shows satisfactory adhesion to the skin and low irritation property. The effects of the present invention can be exerted irrespective of the kind of functional group that the plasticizer and drug may have.

The present invention is described in more detail by way of Examples, to which the invention is not limited. In the following description, "parts" means "parts by weight".

Example 1

2-Ethylhexyl acrylate (75 parts), isobutyl acrylate (20 parts), acrylic acid (5 parts), 1-dodecanethiol (0.06 part) and ammonium peroxodisulfate (0.2 part) were subjected to emulsion polymerization in an aqueous solution to give an alkyl acrylate type adhesive (weight average molecular weight, 5,000,000). This adhesive (60 parts) and isopropyl myristate (40 parts) were mixed in ethyl acetate to give a solution for an adhesive layer. This solution was applied onto a polyester separator so that the thickness after drying became 60 μm, and dried at 100° C. for 3 minutes to give an adhesive layer. This adhesive layer was transferred to a nonwoven side of a laminate film of a polyester nonwoven fabric (8 g/m$^2$)/polyester film (2 μm thickness to give a medical adhesive sheet.

Comparative Example 1

2-Ethylhexyl acrylate (75 parts), isobutyl acrylate (20 parts), acrylic acid (5 parts) and azobisisobutyronitrile (0.2 part) were subjected to solution polymerization in ethyl acetate under an inert gas atmosphere, to give an alkyl acrylate adhesive (weight average molecular weight, 1,800, 000). This adhesive (60 parts ) and isopropyl myristate (40 parts ) were mixed in ethyl acetate to give a solution for an adhesive layer. This solution was treated in the same manner as in Example 1 to give a medical adhesive sheet.

Comparative Example 2

In the same manner as in Example 1 except this isopropyl myristate was not sued, a medical adhesive sheet was obtained.

Comparative Example 3

In the same manner as in comparative Example 1 except that isopropyl myristate was not sued, a medical adhesive sheet was obtained.

Reference Example

The adhesive (50 parts ) obtained in Comparative Example 1, trifunctional isocyanate (0.2 part, trademark CORONATE HL, manufactured by NIPPON POLYURETHANE INDUSTRY CO., LTD.) and isopropyl myristate (40 parts)were mixed in ethyl acetate to give a solution for an adhesive layer. This solution was treated in the same manner as in example 1 to give a medical adhesive sheet.

Example 2

The adhesive (50 parts ) obtained in Example 1, isopropyl myristate (40 parts) and metoprolol (10 parts) were mixed in ethyl acetate to give a solution for an adhesive layer. This solution was treated in the same manner as in Example 1 to give a medical adhesive sheet.

Comparative Example 4

The adhesive (50 parts) obtained in Comparative Example 1, isopropyl myristate (40 parts ) and metoprolol (10 parts ) were mixed in ethyl acetate to give a solution for an adhesive layer. This solution was treated in the same manner as in Example 1 to give a medical adhesive sheet.

Comparative Example 5

The adhesive (90 parts ) obtained in Example 1 and metoprolol (10 parts) were mixed in ethyl acetate to give a solution for an adhesive layer. This solution was treated in the same manner as in Example 1 to give a medical adhesive sheet.

Comparative Example 6

The adhesive (50 parts ) obtained in Comparative Example 1, trifunctional isocyanate (0.4 part, trademark CORONATE HL, manufactured by NIPPON POLYURETHANE INDUSTRY CO., LTD.), isopropyl myristate (40 parts) and metoprolol metoprolol (10 parts) were mixed in ethyl acetate to give a solution for an adhesive layer. This solution was treated in the same manner as in Example 1 to give a medical adhesive sheet.

Example 3

2-Ethylhexyl acrylate (75 parts), isobutyl acrylate (20 parts), acrylic acid (5 parts), 1-dodecanethiol (0.06 part) and ammonium peroxodisulfate (0.1 part) were subjected to emulsion polymerization in an aqueous solution to give an alkyl acrylate adhesive (weight average molecular weight, 7,000,000). This adhesive (60 parts) and isopropyl myristate (40 parts) were mixed in ethyl acetate to give a solution for an adhesive layer. This solution was treated in the same manner as in Example 1 to give a medical adhesive sheet.

Comparative Example 7

In the same manner as in Example 3 except that isopropyl myristate was not used, a medical adhesive sheet was obtained.

Example 4

2-Ethylhexyl acrylate (75 parts), isobutyl acrylate (20 parts), acrylic acid (5 parts), 1-dodecanethiol (0.06 part) and ammonium peroxodisulfate (0.4 part) were subjected to emulsion polymerization in an aqueous solution to give an alkyl acrylate type adhesive (weight average molecular weight, 2,500,000). This adhesive (60 parts) and isopropyl myristate (40 parts) were mixed in ethyl acetate to give a solution for an adhesive layer. This solution was treated in the same manner as in Example 1 to give a medical adhesive sheet.

Comparative Example 8

In the same manner as in Example 4 except that isopropyl myristate was not used, a medical adhesive sheet was obtained.

Example 5

The adhesive (50 parts) obtained in Example 3, isopropyl myristate (40 parts) and metoprolol (10 parts) were mixed in ethyl acetate to give a solution for an adhesive layer. This solution was treated in the same manner as in Example 1 to give a medical adhesive sheet.

Example 6

The adhesive (50 parts) obtained in Example 4, isopropyl myristate (40 parts) and metoprolol (10 parts) were mixed in ethyl acetate to give a solution for an adhesive layer. This solution was treated in the same manner as in Example 1 to give a medical adhesive sheet.

Comparative Example 9

The adhesive (90 parts) obtained in Example 3 and metoprolol (10 parts) were mixed in ethyl acetate to give a solution for an adhesive layer. This solution was treated in the same manner as in Example 1 to give a medical adhesive sheet.

Comparative Example 10

The adhesive (90 parts) obtained in Example 4 and metoprolol (10 parts) were mixed in ethyl acetate to give a solution for an adhesive layer. This solution was treated in the same manner as in Example 1 to give a medical adhesive sheet.

Experimental Example 1

The medical adhesive sheets obtained in the above-mentioned Examples 1 to 6, Comparative Examples 1 to 10 and a medical adhesive sheet obtained in Reference Example (those containing CORONATE HL were used upon storage at 70° C. for 2 days) were subjected to the following test.

1. Adhesion to the skin

The samples (10 cm$^2$) obtained in Examples 1 to 6, Comparative Examples 1 to 10 and Reference Example were adhered to the inner side of the upper arm of 6 volunteered test subjects. After 24 hours, adhesion of the samples to the skin was visually observed. A medical adhesive sheet most tightly adhered to the skin was rate 5 and a medical adhesive sheet easily peeled off from the skin was rate 1. The results are shown in Table 1.

TABLE 1

| | Adhesion to skin | | | | | | |
|---|---|---|---|---|---|---|---|
| | 1 | 2 | 3 | 4 | 5 | 6 | average |
| Ex. 1 | 5 | 5 | 5 | 5 | 5 | 5 | 5 |
| Com.Ex.1 | 2 | 1 | 1 | 2 | 1 | 1 | 1 |
| Com.Ex.2 | 5 | 5 | 5 | 5 | 5 | 5 | 5 |
| Com.Ex.3 | 5 | 5 | 5 | 5 | 5 | 5 | 5 |
| Ref.Ex. | 5 | 5 | 5 | 5 | 5 | 5 | 5 |
| Ex. 2 | 5 | 5 | 5 | 5 | 5 | 5 | 5 |

TABLE 1-continued

| | Adhesion to skin | | | | | | |
|---|---|---|---|---|---|---|---|
| | 1 | 2 | 3 | 4 | 5 | 6 | average |
| Com.Ex.4 | 1 | 1 | 1 | 1 | 1 | 1 | 1 |
| Com.Ex.5 | 5 | 5 | 5 | 5 | 5 | 5 | 5 |
| Com.Ex.6 | 1 | 1 | 1 | 1 | 1 | 1 | 1 |
| Ex. 3 | 4 | 5 | 5 | 5 | 4 | 5 | 5 |
| Com.Ex.7 | 4 | 4 | 5 | 5 | 4 | 4 | 4 |
| Ex. 4 | 4 | 5 | 5 | 5 | 5 | 5 | 5 |
| Com.Ex.8 | 3 | 4 | 5 | 5 | 4 | 4 | 4 |
| Ex. 5 | 4 | 5 | 5 | 5 | 5 | 5 | 5 |
| Ex. 6 | 5 | 5 | 4 | 4 | 5 | 5 | 5 |
| Com.Ex.9 | 4 | 4 | 4 | 4 | 5 | 5 | 4 |
| Com.Ex.10 | 5 | 5 | 5 | 4 | 4 | 5 | 5 |

From Table 1, it is apparent that the medical adhesive sheets of Examples 1 to 6 showed superior adhesion to the skin. However, the medical adhesive sheets of Comparative Examples 1 and 4 showed poor cohesion of the adhesive, so that isopropyl myristate was not retained in the adhesive layer and bloomed in the separator interface, thus losing adhesion property. In the medical adhesive sheet of Comparative Example 6, the drug, metoprolol, and CORONATE HL (crosslinking agent) reacted preferentially, so that isopropyl myristate was not retained in the adhesive layer and bloomed in the separator interface, thus losing adhesion property.

2. Keratin peel off

The 12 mm wide, 50 mm long samples were adhered to the inner side of the upper arm of 6 volunteered test subjects and stood for 6 hours. The samples were peeled off and immersed for 24 hours in a dye liquid having the following composition. After washing with distilled water the keratin cells peeled off were stained. The dye liquid used for this test permeated into the nonwoven fabric constituting the support. Thus, a 12 μm thick polyester film was used as a support to give a medical adhesive sheet and the medical adhesive sheet was subjected to the test. Since the medical adhesive sheets of Examples 2, 5 and 6 and Comparative Examples 4–6, 9 and 10 contained a drug for percutaneous absorption (metoprolol), the same placebo medical adhesive sheets without metoprolol were prepared and subjected to the test.

The stained samples were cut into 12 mm×5 mm pieces and immersed in a 1% aqueous sodium dodecylsulfate solution (5 ml) for 24 hours. The keratin cells adhered to the samples were subjected to color extraction, and absorbance (595 nm) of the extract was determined by a spectrophotometer. As a sample for comparison, a medical adhesive sheet free of adhesion to the skin surface was subjected to the same extraction operation and absorbance determination (595 nm). The difference in the absorbance between the above samples and the sample for comparison was taken as the amount of keratin cells peeled off. The results are shown in Table 2. A greater amount of the peeled keratin cells makes the absorbance higher. The absorbance is preferably not more than 1.0, particularly not more than 0.5. A fine correlation was found between the absorbance and the number of cells peeled off as counted with a stereoscopic microscope. <composition of dye liquid>

| | | |
|---|---|---|
| | Gentian Violet | 1.0% |
| | Brillian Green | 0.5% |
| | Distilled water | 98.5% |

3. Degree of pain

Each sample was cut into 10 cm² pieces and adhered to the inner side of the upper arm of 6 volunteered test subjects and stood for 1 hour. The sample was peeled off and the pain upon peeling off was evaluated. The evaluation was based on the following criteria, and the average was determined. The results are shown in Table 2.

TABLE 2

| Sample | Keratin peel-off amount (ABS) | Degree of pain |
|---|---|---|
| Ex. 1 | 0.35 | 1 |
| Com.Ex.1 | *1 | *2 |
| Com.Ex.2 | 1.42 | 3 |
| Com.Ex.3 | 1.25 | 5 |
| Ref.Ex. | 0.34 | 1 |
| Ex. 2 | 0.36 | 1 |
| Com.Ex.4 | *1 | *2 |
| Com.Ex.5 | 1.41 | 3 |
| Com.Ex.6 | *1 | *2 |
| Ex. 3 | 0.38 | 1 |
| Com.Ex.7 | 1.55 | 4 |
| Ex. 4 | 0.26 | 1 |
| Com.Ex.8 | 1.62 | 5 |
| Ex. 5 | 0.24 | 1 |
| Ex. 6 | 0.32 | 1 |
| Com.Ex.9 | 1.25 | 4 |
| Com.Ex.10 | 1.41 | 4 |

*1 : determination not possible due to blooming
*2 : not determined due to *1
1 : no pain
2 : pain was felt
3 : slightly painful
4 : painful
5 : very painful From Table 2, it is apparent that the medical adhesive sheets of Examples 1–6 showed small amount of keratin peeled off ad caused less pain upon peeling. In contrast, the medical adhesive sheets of Comparative Examples 2, 3, 5 and 7–10 showed greater amounts of keratin peeled off and caused pain upon peeling. The medical adhesive sheets of Comparative Examples 1, 4 and 6 suffered from blooming in the separator interface and the measurement was not possible.

4. Transfer to skin

The samples (10 cm²) of Examples 2, 5 and 6, and Comparative Examples 4–6, 9 and 10 were adhered to the inner side of the upper arm of a person for 8 hours. After peeling, metoprolol was extracted from the adhesive sheet with methanol and quantitatively determined by HPLC (detector UV 210 nm). The drug in the sample free to adhesion was taken as 100%, and the percentage of transfer to human skin was calculated from the measurement values. The transfer percentage was preferably not less than 10%, particularly not less than 30%.

TABLE 3

| Sample | Transfer (%) |
|---|---|
| Ex.2 | 35 |
| Comp.Ex.4 | *3 |
| Comp.Ex.5 | 12 |
| Comp.Ex.6 | *3 |
| Ex.5 | 29 |
| Ex.6 | 38 |
| Comp.Ex.9 | 8 |
| Comp.Ex.10 | 15 |

*3 : determination not possible

From Table 3, the medical adhesive sheets of Examples 2, 5 and 6 showed fine transfer percentages. In comparison with these Examples, the medical adhesive sheets of Comparative Examples 5, 9 and 10 showed inferior transfer percentages. The residual adhesive and isopropyl myristate of the medical adhesive sheets of Comparative Examples 4 and 6 were found on the adhesion site on the arm, thus making the measurement unattainable. (Preparation of acrylic copolymer A)

2-Ethylhexyl acrylate (75 parts), isobutyl acrylate (20 parts), acrylic acid (5 parts), 1-dodecanethiol (0.06 part) and ammonium peroxodisulfate (0.2 part) were subjected to emulsion polymerization in an aqueous solution to give an acrylic copolymer a solution (weight average molecular weight, 2,000,000). (Preparation of acrylic copolymer B)

2-Ethylhexyl acrylate (75 parts), acrylic acid (5 parts) and azobisisobutyronitrile (0.2 part) were subjected to solution polymerization in ethyl acetate under an inert gas atmosphere, to give an acrylic copolymer B solution (weight average molecular weight, 1,500,000).

Examples 7–10

Comparative Examples 11–17

According to the compositions shown in Table 4, a solution for an adhesive layer was prepared and this solution was applied to a polyester separator so that the thickness after drying was 60 μm, which was dried at 100° C. for 5 minutes to give an adhesive layer. This adhesive layer was transferred onto the nonwoven surface of a laminate film of a polyester nonwoven fabric (8g/m²)/polyester film (2 μm thickness) to give a medical adhesive sheet.

TABLE 4

| Sample | Copoly-mer (%) | Liquid compo-nent (%) | Solid compo-nent (%) | Meto-prolol (%) | Notes |
| --- | --- | --- | --- | --- | --- |
| Ex.7 | A 60 | IPM35 | GMC 5 | — | |
| Ex.8 | A 60 | IPM30 G2 CA 3 | GMC 5 | — | |
| Com.Ex.11 | B 60 | IPM35 | GMC 5 | — | cohesive failure |
| Com.Ex.12 | B 60 | IPM30 G2 CA3 | GMC 5 | — | cohesive failure |
| Com.Ex.13 | B 75 | IPM15 G2 CA3 | GMC 5 | — | |
| Ex.9 | A 55 | IPM35 | GMC 5 | 5 | |
| Ex.10 | A 55 | IPM30 G2 CA3 | GMC 5 | 5 | |
| Com.Ex.14 | B 55 | IPM35 | GMC 5 | 5 | cohesive failure |
| Com.Ex.15 | B 55 | IPM30 G2 CA3 | GMC 5 | 5 | cohesive failure |
| Com.Ex.16 | B 70 | IPM14 G2 CA3 | GMC 5 | 5 | |
| Com.Ex.17 | B 60 | IPM25 G2 CA3 | GMC 5 | 5 | addition of crosslinking agent, cohesive failure |

IPM : isopropyl myristate
G : glycerol
CA : caprylic acid
GMC : glyceryl monocaprylate
Crosslinking agent : CORONATE HL (trifunctional isocyanate) 1% addition to solid adhesive Experimental Example 2

The medical adhesive sheets obtained in the above-mentioned Examples 7 to 10 and Comparative Examples 11 to 17 (those containing CORONATE HL were used upon preservation at 70° C. for 2 days) were subjected to the same test as in Experimental Examples 1. The results are shown in Table 5.

TABLE 5

| | Ad-hesion to skin | Keratin peel off (ABS) | Degree of pain | Transfer (%) |
| --- | --- | --- | --- | --- |
| Ex.7 | 5 | 0.31 | 1 | — |
| Ex.8 | 5 | 0.29 | 1 | — |
| Com.Ex.11 | 1 | unmeasurable | unmeasurable | — |
| Com.Ex.12 | 1 | unmeasurable | unmeasurable | — |
| Com.Ex.13 | 4 | 0.82 | 4 | — |
| Ex.9 | 5 | 0.25 | 1 | 27 |
| Ex.10 | 5 | 0.32 | 1 | 35 |
| Com.Ex.14 | 1 | unmeasurable | unmeasurable | unmeasurable |
| Com.Ex.15 | 1 | unmeasurable | unmeasurable | unmeasurable |
| Com.Ex.16 | 4 | 0.76 | 3 | 10 |
| Com.Ex.17 | 1 | unmeasurable | unmeasurable | unmeasurable |

1. Adhesion to skin

From Table 5, it is apparent that the medical adhesive sheets of Examples 7–10 and Comparative Examples 13 and 16 showed superior adhesion to the skin. However, the medical adhesive sheets of Comparative Examples 11, 12, 14 and 15 showed poor cohesion of the adhesive polymer, so that isopropyl myristate was not retained in the adhesion layer but bloomed in the separator interface, thus losing adhesion property. In the medical adhesive sheet of Comparative Examples 17, the drug, metoprolol, and CORONATE HL (crosslinking agent) reacted preferentially, so that isopropyl myristate was not retained in the adhesive layer but bloomed in the separator interface, thus losing adhesion property.

2. Keratin peel off and degree of pain

From Table 5, the medical adhesive sheets of Examples 7 to 10 showed less peeling of keratin and less pain upon peeling. However, the medical adhesive sheets of Comparative Examples 13 and 16 showed greater amounts of keratin peeling and caused pain upon peeling. The medical adhesive sheets of Comparative Examples 11, 12, 14, 15 and 17 suffered from blooming in the separator interface and measurement was not attainable.

3. Transfer to the skin

From Table 5, the medical adhesive sheets of examples 9 and 10 showed find transfer percentages, but when compared with these Examples, the medical adhesive sheets of Comparative Example 16 showed a poor transfer percentage. The residual adhesive and isopropyl myristate of the medical adhesive sheets of Comparative Examples 14, 15 and 17 were found on the adhesion site on the arm and the measurement was not attainable.

As is evident from the foregoing explanation, the present invention enables superior retention of a plasticizer in the adhesive layer even without a crosslinking treatment. Consequently, a medical adhesive sheet capable of satisfying both the fine adhesion to the skin and low irritation to the skin can be provided. The effects of the present invention can be exerted irrespective of the kind of functional group that the plasticizer and drug have.

The present applications based on application Nos. 192894/1997 and 195375/1998 filed in Japan, the contents of which are incorporated hereinto by reference.

What is claimed is:

1. A medical adhesive sheet comprising a support and an adhesive layer formed on one side of said support, wherein the adhesive layer comprises an adhesive polymer having a weight average molecular weight of not less than 2,500,000 and at least one plasticizer compatible with said polymer.

2. The medical adhesive sheet of claim 1, wherein the adhesive polymer has a weight average molecular weight of not less than 5,000,000.

3. The medical adhesive sheet of claim 1, wherein the adhesive polymer is an acrylate type polymer.

4. The medical adhesive sheet of claim 3, wherein the acrylate type polymer is a copolymer obtained by copolymerizing alkyl (meth)acrylate as a main component.

5. The medical adhesive sheet of claim 1, wherein the plasticizer is a liquid plasticizer.

6. The medical adhesive sheet of claim 5, wherein the liquid plasticizer is contained in a proportion of 10–100 parts by weight per 100 parts by weight of the adhesive polymer.

7. The medical adhesive sheet of claim 5, wherein the liquid plasticizer is a fatty acid ester comprising a higher fatty acid having 12 to 16 carbon atoms and a lower monovalent alcohol having 1 to 4 carbon atoms.

8. The medical adhesive sheet of claim 1, wherein the plasticizer comprises a liquid plasticizer and a solid plasticizer.

9. The medical adhesive sheet of claim 8, wherein the liquid plasticizer is contained in a proportion of 10–100 parts by weight per 100 parts by weight of the adhesive polymer.

10. The medical adhesive sheet of claim 8, wherein the liquid plasticizer is a fatty acid ester comprising a higher fatty acid having 12 to 16 carbon atoms and a lower monovalent alcohol having 1 to 4 carbon atoms, or a combination of said fatty acid ester, a fatty acid having 8 to 10 carbon atoms and glycerol.

11. The medical adhesive sheet of claim 8, wherein the solid plasticizer is contained in a proportion of not more than 10 parts by weight per 100 parts by weight of the adhesive polymer.

12. The medical adhesive sheet of claim 8, wherein the solid plasticizer is a monoglyceride comprising a fatty acid having 8 to 10 carbon atoms and glycerol.

13. The medical adhesive sheet of claim 1, wherein the adhesive layer further contains a drug for percutaneous absorption.

14. A method for producing a medical adhesive sheet, which comprises (a) applying a solution containing a composition comprising an adhesive polymer having a weight average molecular weight of not less than 2,500,000 and at least one plasticizer compatible with said polymer on one surface of a support and (b) drying same to form an adhesive layer.

15. The method of claim 14, wherein the adhesive polymer is prepared by emulsion polymerization.

16. The medical adhesive sheet of claim 1, wherein the adhesive layer is not cross-linked.

17. The method of claim 14, wherein the adhesive layer is not cross-linked.

* * * * *